United States Patent [19]

Vogelstein et al.

[11] Patent Number: 5,411,860
[45] Date of Patent: May 2, 1995

[54] AMPLIFICATION OF HUMAN MDM2 GENE IN HUMAN TUMORS

[75] Inventors: Bert Vogelstein; Kenneth W. Kinzler, both of Baltimore, Md.

[73] Assignee: The Johns Hopkins University, Baltimore, Md.

[21] Appl. No.: 903,103

[22] Filed: Jun. 23, 1992

Related U.S. Application Data

[63] Continuation-in-part of Ser. No. 867,840, Apr. 7, 1992, abandoned.

[51] Int. Cl.⁶ .......................... C12Q 1/68; C12P 19/34
[52] U.S. Cl. ................................. 435/6; 435/91.2; 436/813
[58] Field of Search .............. 435/6, 91.2; 935/77; 436/813

[56] References Cited

PUBLICATIONS

Romkes et al. Biochemistry 30:3247-3255 (1991) "Cloning & Expression of CDNA for . . . ".
Fakharzadeh, et al., "Tumorigenic Potential Associated with Enhanced Expression of a Gene That is Amplified in a Mouse Tumor Cell Line", *The EMBO Journal*, 10(6):1565-1569 (1991).
Hinds, et al., "Mutant p53 DNA Clones From Human Colon Carcinomas Cooperate With Ras in Transforming Primary Rat Cells: A Comparison of the Hot Spot Mutant Phenotypes", *Cell Growth & Differentiation*, 1:561-580 (1990).
Oliner, et al., "Amplification of a Gene Encoding a p53-Associated Protein in Human Sarcomas," *Nature*, 358:80-83 (1992).
Oliner, et al., "Oncoprotein MDM2 Conceals the Activation Domain of Tumour Suppressor p53", *Nature*, 362(6423):857-860 (1993), abstract.
Leach et al., "p53 Mutation and MDM2 Amplification in Human Soft Tissue Sarcomas," *Cancer Research*, 53:2231-2234 (1993).
Momand, et al., "The mdm-2 Oncogene Product Forms a Complex With the p53 Protein and Inhibits p53-Mediated Transactivation," *Cell*, 69:1237-1245 (1992).

*Primary Examiner*—Margaret Parr
*Assistant Examiner*—Eggerton Campbell
*Attorney, Agent, or Firm*—Banner, Birch, McKie & Beckett

[57] ABSTRACT

A human gene has been discovered which is genetically altered in human tumor cells. The genetic alteration is gene amplification and leads to a corresponding increase in gene products. Detecting that the gene, designated hMDM2, has become amplified or detecting increased expression of gene products is diagnostic of tumorigenesis. Human MDM2 protein binds to human p53 and appears to allow the cell to escape from p53-regulated growth.

12 Claims, 12 Drawing Sheets

FIG. IA(1)

```
  1    GCACCGCGCGAGCTTGGCTGCTTCTGGGGC

*  AG
 84    GGCCGCGACCCCTCTGACCGAGATCCTGCTG

CGT  GC  GG  CTCCGCGCTCCCCG GAAG
168    GTGCCCTGGCCCGGAGAGTGGAATGATCCCC

ACC GACACCCCTGGGGACC    TCG AT
252    GGAGTCTTGAGGGACCCCGACTCCAAGCGC
  1

T     C  G         C    G
336    CCTACTGATGGTGCTGTAACCACCTCACAGA
  9    P   T   D   G   A   V   T   T   S   Q
       S       E       A   S

G             C       A   G       C
420    TTATTAAAGTCTGTTGGTGCACAAAAAGACA
 37    L   L   K   S   V   G   A   Q   K   D
                                           N

A G             C             G G   C
504    CGATTATATGATGAGAAGCAACAACATATTG
 65    R   L   Y   D   E   K   Q   Q   H   I

G                         G  A
588    GTGAAAGAGCACAGGAAAATATATACCATGA
 93    V   K   E   H   R   K   I   Y   T   M
                                           A

GC         G    AC      G  C
672    TCTGTGAGTGAGAACAGGTGTCACCTTGAAG
121    S   V   S   E   N   R   C   H   L   E
           L           S       R   Q   P
```

FIG. 1A(2)

```
CTGTGTGGCCCTGTGTGTCGGAAAGATGGAGCAAGA

AGCCGC GC TTCTC TCG TCGAGCT TG ACGAC
CTTTCGCAGCCAGGAGCACCGTCCCTCCCCGGATTA

GTCGGAA ATGCGC G AAGTAG    CC    T CT
GAGGCCCAGGGCGTCGTGCTTCCGCAGTAGTCAGTC

ACCGCG TTCTCCT C GCCTC       C
GAAAACCCCGGATGGTGAGGAGCAGGCAAATGTGCA
                                M  C

T
TTCCAGCTTCGGAACAAGAGACCCTGGTTAGACCAA
 I   P   A   S   E   Q   E   T   L   V   R   P

C           A   A   A      A
CTTATACTATGAAAGAGGTTCTTTTTTATCTTGGCC
 T   Y   T   M   K   E   V   L   F   Y   L   G
             I   I               I

G                   C           G
TATATTGTTCAAATGATCTTCTAGGAGATTTGTTTG
 V   Y   C   S   N   D   L   L   G   D   L   F
                                         V

A  T   A   G CT A G        A----
TCTACAGGAACTTGGTAGTAGTCAATCAGCAGGAAT
 I   Y   R   N   L   V   V   V   N   Q   Q   E
                         A       S           -

TG       T C T  G       C  CA
GTGGAGTGATCAAAAGGACCTTGTACAAGAGCTTC
 G   G   S   D   Q   K   D   L   V   Q   E   L
 L               P       L       A       P
```

FIG. 1A(3)

| | | |
|---|---|---|
| AGCCGAGCCCGAGGGGC | 83 | Human nt |
| | | |
| CATG　CGCTCA　G　C | | Mouse nt |
| GTGCGTACGAGCGCCCA | 167 | Human nt |
| | | |
| GGGCGAGC　GAGACC | | Mouse nt |
| CCCGTGAAGGAAACTGG | 251 | Human nt |
| | | |
| 　　　　　　　　G | | Mouse nt |
| ATACCAACATGTCTGTA | 335 | Human nt |
| N　T　N　M　S　V | 8 | Human a.a. |
| | | Mouse a.a. |
| | | |
| A | | Mouse nt |
| AGCCATTGCTTTTGAAG | 419 | Human nt |
| K　P　L　L　L　K | 36 | Human a.a. |
| | | Mouse a.a. |
| | | |
| 　　　　　　　G | | Mouse nt |
| AGTATATTATGACTAAA | 503 | Human nt |
| Q　Y　I　M　T　K | 64 | Human a.a. |
| | | Mouse a.a. |
| | | |
| 　A　C　G　T | | Mouse nt |
| GCGTGCCAAGCTTCTCT | 587 | Human nt |
| G　V　P　S　F　S | 92 | Human a.a. |
| | | Mouse a.a. |
| | | |
| -----　　T　C | | Mouse nt |
| CATCGGACTCAGGTACA | 671 | Human nt |
| S　S　D　S　G　T | 120 | Human a.a. |
| -　- | | Mouse a.a. |
| | | |
| CA | | Mouse nt |
| AGGAAGAGAAACCTTCA | 755 | Human nt |
| Q　E　E　K　P　S | 148 | Human a.a. |
| P | | Mouse a.a. |

FIG. 1B(1)

```
              TG       AA              TG
756   TCTTCACATTTGGTTTCTAGACCATCT
149    S   S   H   L   V   S   R   P   S
               D       I           L

G    G    G    CC  G    G       G  GG
840   GGTGAACGACAAAGAAAACGCCACAAA
177    G   E   R   Q   R   K   R   H   K
                   H               R   R

G    CAGCGGCGGCACGAGCA  CAGT
924   ATATGT----------------TGTGAA
205    I   C   -   -   -   -   -   C   E
       M       S   G   G   T   S   S   S

G        T             CC
993   GTAAGTGAACATTCAGGTGATTGGTTG
228    V   S   E   H   S   G   D   W   L
                                       C

G        C        G        C
1077  TCAGAAGATTATAGCCTTAGTGAAGAA
256    S   E   D   Y   S   L   S   E   E
                                       D

A    A    C          C   T
1161  GGGGAGAGTGATACAGATTCATTTGAA
284    G   E   S   D   T   D   S   F   E

T                 C    A
1245  AATCCCCCCTTCCATCACATTGCAAC
312    N   P   P   L   P   S   H   C   N
                                       K

A
1329  GAAATCTCTGAGAAAGCCAAACTGGAA
340    E   I   S   E   K   A   K   L   E
```

FIG. 1B(2)

```
                T C                                    G
     ACCTCATCTAGAAGGAGAGCAATTAGTGAGACAGAAGAA
      T   S   S   R   R   A   I   S   E   T   E   E
                          S

------------    G             CCG        G
     TCTGATAGTATTTCCCTTTCCTTTGATGAAAGCCTGGCT
      S   D   S   I   S   L   S   F   D   E   S   L   A
      -   -   -   -                   P           G

C       C       C   G   C       A       C   C
     AGAAGCAGTAGCAGTGAATCTACAGGGACGCCATCGAAT
      R   S   S   S   S   E   S   T   G   T   P   S   N
      S                               E               H

T                 C   G
     GATCAGGATTCAGTTTCAGATCAGTTTAGTGTAGAATTT
      D   Q   D   S   V   S   D   Q   F   S   V   E   F

G   C   G           G           C       GG
     GGACAAGAACTCTCAGATGAAGATGATGAGGTATATCAA
      G   Q   E   L   S   D   E   D   D.  E   V   Y   Q
          H                                           R

G              G                              G   T
     GAAGATCCTGAAATTTCCTTAGCTGACTATTGGAAATGC
      E   D   P   E   I   S   L   A   D   Y   W   K   C
      G

C   A                    C        A   C
     AGATGTTGGGCCCTTCGTGAGAATTGGCTTCCTGAAGAT
      R   C   W   A   L   R   E   N   W   L   P   E   D
              T                                        D

G T   G       A         G           G
     AACTCAACACAAGCTGAAGAGGGCTTTGATGTTCCTGAT
      N   S   T   Q   A   E   E   G   F   D   V   P   D
      A                           L
```

FIG. 1B(3)

```
       CA        GC   C                    Mouse nt
   AATTCAGATGAATTATCT          839         Human nt
     N  S  D  E   L   S        176         Human a.a.
        T            P                     Mouse a.a.

AGC G                           Mouse nt
   CTGTGTGTAATAAGGGAG           923        Human nt
     L  C  V  I   R   E         204        Human a.a.
           E  L                             Mouse a.a.

A         C  A     C                  Mouse nt
   CCGGATCTTGATGCTGGT            992       Human nt
     P  D  L  D   A   G         227        Human a.a.
     Q            D                         Mouse a.a.

G       G                     Mouse nt
   GAAGTTGAATCTCTCGAC           1076        Human nt
     E  V  E  S   L   D         255        Human a.a.
                                            Mouse a.a.

C   A  C         A                  Mouse nt
   GTTACTGTGTATCAGGCA           1160       Human nt
     V  T  V  Y   Q   A         283        Human a.a.
                      T                     Mouse a.a.

C                                   Mouse nt
   ACTTCATGCAATGAAATG           1244       Human nt
     T  S  C  N   E   M         311        Human a.a.
                                            Mouse a.a.

G              T                    Mouse nt
   AAAGGGAAAGATAAAGGG           1228       Human nt
     K  G  K  D   K   G         339        Human a.a.
                      V                     Mouse a.a.

G C       GCTG C   A                   Mouse nt
   TGTAAAAAAACTATAGTG           1412       Human nt
     C  K  K  T   I   V         367        Human a.a.
     G         L  T   E                     Mouse a.a.
```

FIG. IC(1)

```
              G T A     C       C           G
1413    AATGATTCCAGAGAGTCATGTGTTGAGGAA
 368      N D S R E   S   C   V E E
              A K     P       A

C   A     G       C C           G
1494    TCTCAGCCATCAACTTCTAGTAGCATTATT
 395      S Q P S T S S S I I
                                              V

C                 C CT          G
1578    GAAGAGAGTGTGGAATCTAGTTTGCCCCTT
 423      E E S V E S S   L P L
          D                   F S

T C       G T     C C     T A
1662    GTCCATGGCAAAACAGGACATCTTATGGCC
 451      V H G K T G H L M A
                                        S

G       C                       G
1746    AGACAACCAATTCAAATGATTGTGCTAACT
 479      R Q P I Q M I V L T
                                          S

1830    TAACCCTAGGAATTTAGACAACCTGAAATT
1914    TTAGTATAATTGACCTACTTTGGTAGTGGA
1998    ACTCCTAATTTTAAATAATTTCTACTCTGT
2082    ATGTAACTTATTATTTTTTTGAGACCGAG
2166    CTCTGCCCTCCCCGGGTTCGCACCATTCTC
2250    TAATTTTTTGTACTTTTAGTAGAGACAGGG
2334    CTCGGCCTCCCAAAGTGCTGGGATTACAGG
```

FIG. IC(2)

```
  G  CAGC   G  G  GGCCGA     GA GC C  TG   C
AAT---GATGATAAAATTACACAAGCTTCACAATCAC
 N  -  D  D  K  I  T  Q  A  S  Q  S
 D  S  E  E     A  E     T  P  L

AGC              G--- A
TATAGCAGCCAAGAAGATGTGAAAGAGTTTGAAAGGG
 Y  S  S  Q  E  D  V  K  E  F  E  R
          S              L  -  K

C      A         C  C  G  G   G
AATGCCATTGAACCTTGTGTGATTTGTCAAGGTCGAC
 N  A  I  E  P  C  V  I  C  Q  G  R

T  C  G              A     A  C
TGCTTTACATGTGCAAAGAAGCTAAAGAAAAGGAATA
 C  F  T  C  A  K  K  L  K  K  R  N

C  AA   C        CTCA A  A   T
TATTTCCCCTAGTTGACCTG---TCTATAAGAGAATT
  Y  F  P
        N
```

TATTCACATATATCAAAGTGAGAAAATGCCTCAATTC
ATAGTGAATACTTACTATAATTTGACTTGAATATGTA
CTTAAATGAGAAGTACTTGGTTTTTTTTTTCTTAAAT
TCTTGCTCTGTTACCCAGGCTGGAGTGCAGTGGGTGA
CTGCCTCAGCCTCCCAATTAGCTTGGCCTACAGTCAT
TTTCACCGTGTTAGCCAGGATGGTCTCGATCTCCTGA
CATGAGCCACCG

FIG. 1C(3)

```
     G    G       C                          Mouse nt
   AAGAAAGTGAAGACTAT         1493            Human nt
     Q    E    S    E    D    Y    394       Human a.a.
                    D                         Mouse a.a.

G         G   GC                        Mouse nt
   AAGAAACCCAAGACAAA          1577            Human nt
     E    E    T    Q    D    K    422       Human a.a.
                    H                         Mouse a.a.

C                               Mouse nt
   CTAAAAATGGTTGCATT          1661            Human nt
     P    K    N    G    C    I    450       Human a.a.
                                              Mouse a.a.

G    C                    Mouse nt
   AGCCCTGCCCAGTATGT          1745            Human nt
     K    P    C    P    V    C    478       Human a.a.
                                              Mouse a.a.

T                   *                      Mouse nt
   ATATATTTCTAACTATA          1829            Human nt
                                    491       Human a.a.
                                              Mouse a.a.

ACATAGATTTCTTCTCT          1913            Human nt
   GCTCATCCTTTACACCA          1997            Human nt
   ATGTATATGACATTTAA          2081            Human nt
   TCTTGGCTCACTGCAAG          2165            Human nt
   CTGCCACCACACCTGGC          2249            Human nt
   CCTCGTGATCCGCCCAC          2333            Human nt
                              2372            Human nt
```

AMPLIFICATION OF HUMAN MDM2 GENE IN HUMAN TUMORS

This application is a continuation-in-part of U.S. application Ser. No. 07/867,840, filed on Apr. 7, 1992, which is now abandoned.

FIELD OF THE INVENTION

The invention relates to the area of cancer diagnostics and therapeutics. More particularly, the invention relates to the detection of a gene which is amplified in certain human tumors.

BACKGROUND OF THE INVENTION

According to the Knudson model for tumorigenesis (Cancer Research, 1985, vol. 45, p. 1482), there are tumor suppressor genes in all normal cells which, when they become non-functional due to mutation, cause neoplastic development. Evidence for this model has been found in cases of retinoblastoma and colorectal tumors. The implicated suppressor genes in these tumors, RB and p53 respectively, were found to be deleted or altered in many of the tumors studied.

The p53 gene product, therefore, appears to be a member of a group of proteins which regulate normal cellular proliferation and suppression of cellular transformation. Mutations in the p53 gene have been linked to tumorigenesis, suggesting that alterations in p53 protein function are involved in cellular transformation. The inactivation of the p53 gene has been implicated in the genesis or progression of a wide variety of carcinomas (Nigro et al., 1989, Nature 342:705-708), including human coWrectal carcinoma (Baker et al., 1989, Science 244:217-221), human lung cancer (Takahashi et al., 1989, Science 246:491-494; Iggo et al., 1990, Lancet 335:675-679), chronic myelogenous leukemia (Kelman et al, 1989, Proc. Natl. Acad. Sci. USA 86:6783-6787) and osteogenic sarcomas (Masuda et al., 1987, Proc. Natl. Acad. Sci. USA 84:7716-7719).

While there exists an enormous body of evidence linking p53 gene mutations to human tumorigenesis (Hollstein et al., 1991, Science 253:49-53) little is known about cellular regulators and mediators of p53 function.

Hinds et al. (Cell Growth & Differentiation, 1990, 1:571-580), found that p53 cDNA clones, containing a point mutation at amino acid residue 143, 175, 273 or 281, cooperated with the activated ras oncogene to transform primary rat embryo fibroblasts in culture. These mutant p53 genes are representative of the majority of mutations found in human cancer. Hollstein et al., 1991, Science 253:49-53. The transformed fibroblasts were found to produce elevated levels of human p53 protein having extended half-lives (1.5 to 7 hours) as compared to the normal (wild-type) p53 protein (20 to 30 minutes).

Mutant p53 proteins with mutations at residue 143 or 175 form an oligomeric protein complex with the cellular heat shock protein hsc70. While residue 273 or 281 routants do not detectably bind hsc70, and are poorer at producing transformed foci than the 175 mutant, complex formation between mutant p53 and hsc70 is not required for p53-mediated transformation. Complex formation does, however, appear to facilitate this function. All cell lines transformed with the mutant p53 genes are tumorigenic in athymic (nude) mice. In contrast, the wild-type human p53 gene does not possess transforming activity in cooperation with ras. Tuck and Crawford, 1989, Oncogene Res. 4:81-96.

Hinds et al. supra also expressed human p53 protein in transformed rat cells. When the expressed human p53 was immunoprecipitated with two p53 specific antibodies directed against distinct epitopes of p53, an unidentified $M_r$ 90,000 protein was coimmunoprecipitated. This suggested that the rat $M_r$ 90,000 protein is in a complex with the human p53 protein in the transformed rat cell line.

As mentioned above, levels of p53 protein are often higher in transformed cells than normal cells. This is due to mutations which increase its metabolic stability (Oven et al., 1981, Mol. Cell. Biol. 1:101-110; Reich et al., (1983), Mol. Cell. Biol. 3:2143-2150). The stabilization of p53 has been associated with complex formation between p53 and viral or cellular proteins. (Linzer and Levine, 1979, Cell 17:43-52; Crawford et al., 1981, Proc. Natl. Acad. Sci. USA 78:41-45; Dippold et al., 1981, Proc. Natl. Acad. Sci. USA 78:1695-1699; Lane and Crawford, 1979, Nature (Lond.) 278:261-263; Hinds et al., 1987, Mol. Cell. Biol. 7:2863-2869; Finlay et al., 1988, Mol. Cell. Biol. 8:531-539; Sarnow et al., 1982, Cell. 28:387-394; Gronostajski et al., 1984, Mol. Cell. Biol. 4:442-448; Pinhasi-Kimhi et al., 1986, Nature (Lond.) 320:182-185; Ruscetti and Scolnick, 1983, J. Virol. 46:1022-1026; Pinhasi and Oren, 1984, Mol. Cell. Biol. 4:2180-2186; and Sturzbecher et al., 1987, Oncogene 1:201-211.) For example, p53 protein has been observed to form oligomeric protein complexes with the SV40 large T antigen, the adenovirus type 5 E1B-$M_r$ 55,000 protein, and the human papilloma virus type 16 or 18 E6 product. Linzer and Levine, 1979, Cell 17:43-52; Lane and Crawford, 1979, Nature, 278:261-263; Sarnow et al., 1982, Cell 28:387-394; Werness et al., 1990, Science, 248:76-79. Similarly, complexes have been observed of p105$^{RB}$ (the product of the retinoblastoma susceptibility gene) with T antigen (DeCaprio et al., 1988, Cell 54:275-283), the adenovirus E1A protein (Whyte et al., 1988, Nature 334:124-129) and the E7 protein of human papilloma virus 16 or 18 (Münger et al., 1989, EMBO J. 8:4099-4105). It has been suggested that interactions between these viral proteins and p105$^{RB}$ inactivate a growth-suppressive function of p105$^{RB}$, mimicking deletions and mutations commonly found in the RB gene in tumor cells. In a similar fashion, oligomeric protein complex formation between these viral proteins and p53 may eliminate or alter the function of p53. Finlay et al., 1989, Cell 57:1083-1093.

Fakharzadeh et al. (EMBO J. 1991, 10:1565-1569) analyzed amplified DNA sequences present in a tumorigenic mouse cell line (i.e., 3T3DM, a spontaneously transformed derivative of mouse Balb/c cells). Studies were conducted to determine whether any of the amplified genes induced tumorigenicity following introduction of the amplified genes into a nontransformed recipient cell (e.g., mouse NIH3T3 or Rat2 cells). The resulting cell lines were tested for tumorigenicity in nude mice. A gene, designated MDM2, which is amplified more than 50-fold in 3T3DM cells, induced tumorigenicity when overexpressed in NIH3T3 and Rat 2 cells. From the nucleotide and predicted amino acid sequence of mouse MDM2 (mMDM2), Fakharzadeh speculated that this gene encodes a potential DNA binding protein that functions in the modulation of expression of other genes and, when present in excess, interferes with normal constraints on cell growth.

SUMMARY OF THE INVENTION

It is an object of the invention to provide a method for diagnosing a neoplastic tissue, such as sarcoma, in a human.

It is another object of the invention to provide a cDNA molecule encoding the sequence of human MDM2.

Yet another object of the invention is to provide a preparation of human MDM2 protein which is substantially free of other human cellular proteins.

Still another object of the invention is to provide DNA probes capable of hybridizing with human MDM2 genes or mRNA molecules.

Another object of the invention is to provide antibodies immunoreactive with human MDM2 protein.

Still another object of the invention is to provide kits for detecting amplification or elevated expression of human MDM2.

Yet another object of the invention is to provide methods for identifying compounds which interfere with the binding of human MDM2 to human p53.

A further object of the invention is to provide a method of treating a neoplastic human cell.

It has now been discovered that hMDM2, a heretofore unknown human gene, plays a role in human cancer. The hMDM2 gene has been cloned and the recombinant derived hMDM2 protein shown to bind to human p53 in vitro. hMDM2 has been found to be amplified in some neoplastic cells and the expression of hMDM2-encoded products has been found to be correspondingly elevated in tumors with amplification of this gene. The elevated levels of MDM2 appear to sequester p53 and allow the cell to escape from p53-regulated growth.

BRIEF DESCRIPTION OF THE DRAWINGS

FIG. 1A–C shows the cDNA sequence of human MDM2. In this figure, human and mouse nucleotide and amino acid sequences are compared, the mouse sequence being shown only where it differs from the corresponding human sequence.

DETAILED DESCRIPTION OF THE INVENTION

Figure 2:
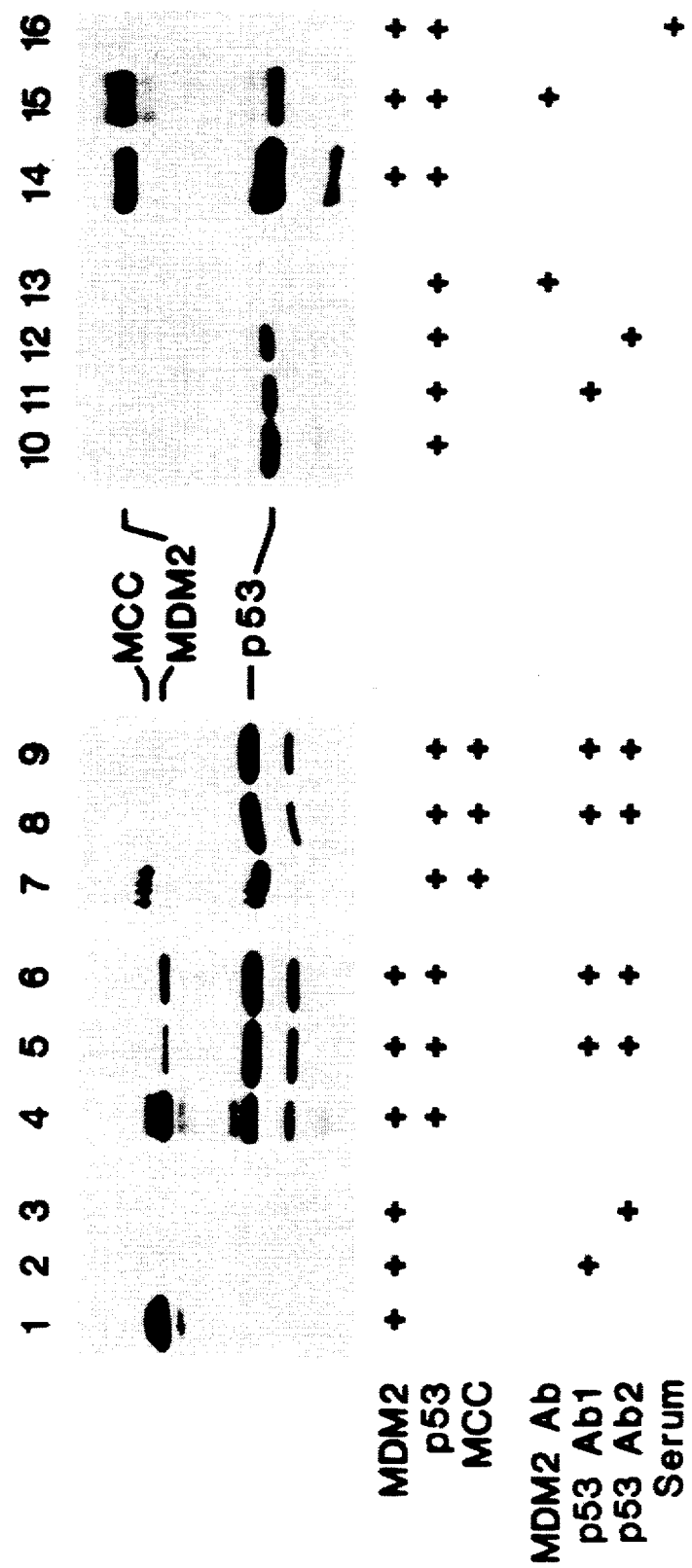
FIG. 2 shows that hMDM2 binds to p53.

It is a discovery of the present invention that a gene exists which is amplified in some human tumors. The amplification of this gene, designated MDM2, is diagnostic of neoplasia or the potential therefor. Detecting the elevated expression of human MDM2-encoded products is also diagnostic of neoplasia or the potential for neoplastic transformation. Over a third of the sarcomas surveyed, including the most common bone and soft tissue forms, were found to have amplified hMDM2 sequences. Expression of hMDM2 was found to be correspondingly elevated in tumors with the gene amplification.

Other genetic alterations leading to elevated hMDM2 expression may be involved in tumorigenesis also, such as mutations in regulatory regions of the gene. Elevated expression of hMDM2 may also be involved in tumors other than sarcomas including but not limited to those in which p53 inactivation has been implicated. These include c,l,rectal carcinoma, lung cancer and chronic myelogenous leukemia.

According to one embodiment of the invention, a method of diagnosing a neoplastic tissue in a human is provided. Tissue or body fluid is isolated from a human, and the copy number of human MDM2 genes is determined. Alternatively, expression levels of human MDM2 gene products can be determined. These include protein and mRNA.

Body fluids which may be tested include urine, serum, blood, feces, saliva, and the like. Tissues suspected of being neoplastic are desirably separated from normal appearing tissue for analysis. This can be done by paraffin or cry, star sectioning or flow cytometry, as is known in the art. Failure to separate neoplastic from non-neoplastic cells can confound the analysis. Adjacent non-neoplastic tissue or any normal tissue can be used to determine a base-line level of expression or copy number, against which the amount of hMDM2 gene or gene products can be compared.

The human MDM2 gene is considered to be amplified if the cell contains more than the normal copy number (2) of this gene per genome. The various techniques for detecting gene amplification are well known in the art. Gene amplification can be determined, for example, by Southern blot analysis, as described in Example 4, wherein cellular DNA from a human tissue is digested, separated, and transferred to a filter where it is hybridized with a probe containing complementary nucleic acids. Alternatively, quantitative polymerase chain reaction (PCR) employing primers can be used to determine gene amplification. Appropriate primers will bind to sequences that bracket human MDM2 coding sequences. Other techniques for determining gene copy number as are known in the art can be used without limitation.

The gene product which is measured may be either mRNA or protein. The term elevated expression means an increase in mRNA production or protein production over that which is normally produced by non-cancerous cells. Although amplification has been observed in human sarcomas, other genetic alterations leading to elevated expression of MDM2 may be present in these or other tumors. Other tumors include those of lung, breast, brain, colorectal, bladder, prostate, liver, skin, and stomach. These, too, are contemplated by the present invention. Non-cancerous cells for use in determining base-line expression levels can be obtained from cells surrounding a tumor, from other humans or from human cell lines. Any increase can have diagnostic value, but generally the mRNA or protein expression will be elevated at least about 3-fold, 5-fold, and in some cases up to about 100-fold over that found in non-cancerous cells. The particular technique employed the detecting mRNA or protein is not critical to the practice of the invention. Increased production of mRNA or protein may be detected, for example, using the techniques of Northern blot analysis or Western blot analysis, respectively, as described in Example 4 or other known techniques such as ELISA, immunoprecipitation, RIA and the like. These techniques are also well known to the skilled artisan.

According to another embodiment of the invention, nucleic acid probes or primers for the determining of human MDM2 gene amplification or elevated expression of mRNA are provided. The probe may comprise ribo- or deoxyribonucleic acids and may contain the entire human MDM2 coding sequence, a sequence complementary thereto, or fragments thereof. A probe may contain, for example, nucleotides 1-949, or 1-2372 as shown in FIG. 1. Generally, probes or primers will contain at least about 14 contiguous nucleotides of the human sequence but may desirably contain about 40, 50 or 100 nucleotides. Probes are typically labelled with a fluorescent tag, a radioisotope, or the like to render them easily detectable. Preferably the probes will hybridize under stringent hybridization conditions. Under such conditions they will not hybridize to mouse MDM2. The probes of the invention are complementary to the human MDM2 gene. This means that they share 100% identity with the human sequence.

hMDM2 protein can be produced, according to the invention, substantially free of other human proteins. Provided with the DNA sequence, those of skill in the art can express the eDNA in a non-human cell. Lysates of such cells provide proteins substantially free of other human proteins. The lysates can be further purified, for example, by immunoprecipitation, coprecipitation with p53, or by affinity chromatography.

The antibodies of the invention are specifically reactive with hMDM2 protein. Preferably, they do not cross-react with MDM2 from other species. They can be polyclonal or monoclonal, and can be raised against native hMDM2 or a hMDM2 fusion protein or synthetic peptide. The antibodies are specifically immunoreactive with hMDM2 epitopes which are not present on other human proteins. Some antibodies are reactive with epitopes unique to human MDM2 and not present on the mouse homolog. The antibodies are useful in conventional analyses, such as Western blot analysis, ELISA and other immunological assays for the detection of proteins. Techniques for raising and purifying polyclonal antibodies are well known in the art, as are techniques for preparing monoclonal antibodies. Antibody binding can be determined by methods known in the art, such as use of an enzyme-labelled secondary antibody, staphylococcal protein A, and the like.

According to another embodiment of the invention, interference with the expression of MDM2 provides a therapeutic modality. The method can be applied in vivo, in vitro, or ex vivo. For example, expression may be downregulated by administering triple-strand forming or antisense oligonucleotides which bind to the hMDM2 gene or mRNA, respectively, and prevent transcription or translation. The oligonucleotides may interact with unprocessed pre-mRNA or processed mRNA. Small molecules and peptides which specifically inhibit MDM2 expression can also be used. Similarly, such molecules which inhibit the binding of MDM2 to p53 would be therapeutic by alleviating the sequestration of p53.

Such inhibitory molecules can be identified by screening for interference of the hMDM2/p53 interaction where one of the binding partners is bound to a solid support and the other partner is labeled. Antibodies specific for epitopes on hMDM2 or p53 which are involved in the binding interaction will interfere with such binding. Solid supports which may be used include any polymers which are known to bind proteins. The support may be in the form of a filter, column packing matrix, beads, and the like. Labeling of proteins can be accomplished according to any technique known in the art. Radiolabels, enzymatic labels, and fluorescent labels can be used advantageously. Alternatively, both hMDM2 and p53 may be in solution and bound molecules separated from unbound subsequently. Any separation technique known in the art may be employed, including immunoprecipitation or immunoaffinity separation with an antibody specific for the unlabeled binding partner.

A eDNA molecule containing the coding sequence of hMDM2 can be used to produce probes and primers. In addition, it can be expressed in cultured cells, such as E. coli, to yield preparations of hMDM2 protein substantially free of other human proteins. The proteins produced can be purified, for example, with immunoaffinity techniques using the antibodies described above.

Kits are provided which contain the necessary reagents for determining gene copy number, such as probes or primers specific for the hMDM2 gene, as well as written instructions. The instructions can provide calibration curves to compare with the determined values. Kits are also provided to determine elevated expression of mRNA (i.e., containing probes) or hMDM2 protein (i.e., containing antibodies). Instructions will allow the tester to determine whether the expression levels are elevated. Reaction vessels and auxiliary reagents such as chromogens, buffers, enzymes, etc. may also be included in the kits.

The human MDM2 gene has now been identified and cloned. Recombinant derived hMDM2 has been shown to bind to human p53. Moreover, it has been found that hMDM2 is amplified in some satcomas. The amplification leads to a corresponding increase in MDM2 gene products. Such amplification is associated with the process of tumorigenesis. This discovery allows specific assays to be performed to assess the neoplastic or potential neoplastic status of a particular tissue.

The following examples are provided to exemplify various aspects of the invention and are not intended to limit the scope of the invention.

EXAMPLE 1

To obtain human cDNA clones, a cDNA library was screened with a murine MDM2 (mMDM2) cDNA probe. A cDNA library was prepared by using polyadenylated RNA isolated from the human colonic carcinoma cell line CaCo-2 as a template for the production of random hexamer primed double stranded cDNA. Gubler and Hoffmann, 1983, Gene 25:263–268. The cDNA was ligated to adaptors and then to the lambda YES phage vector, packaged, and plated as described by Elledge et al. (Proc. Natl. Acad. Sci. USA, 1991, 88:1731–1735). The library was screened initially with a $^{32}$P-labelled (Feinberg and Vogelstein, 1983, Anal. Biochem. 132:6–13) mMDM2 cDNA probe (nucleotides 259 to 1508 (Fakharzadeh et al., 1991, EMBO J. 10:1565–1569)) and then rescreened with an hMDM2 cDNA clone containing nucleotides 40 to 702.

Twelve clones were obtained, and one of the clones was used to obtain thirteen additional clones by rescreening the same library. In total., twenty-five clones were obtained, partially or totally sequenced, and mapped. Sequence analysis of the twenty-five clones revealed several cDNA forms indicative of alternative splicing. The sequence shown in FIG. 1 is representative of the most abundant class and was assembled from three clones: c14-2 (nucleotides 1-949), c89 (nucleotides 467–1737), and c33 (nucleotides 390–2372). The 3' end of the untranslated region has not yet been cloned in mouse or human. The 5' end is likely to be at or near nucleotide 1. There was an open reading frame extending from the 5' end of the human cDNA sequence to nucleotide 1784. Although the signal for translation initiation could not be unambiguously defined, the ATG at nucleotide 312 was considered the most likely position for several reasons. First, the sequence similarity between hMDM2 and mMDM2 fell off dramatically upstream of nucleotide 312. This lack of conservation in an otherwise highly conserved protein suggested that the sequences upstream of the divergence may not code for protein. Second, an anchored polymerase chain reaction (PCR) approach was employed in an effort to acquire additional upstream cDNA sequence. Ochman et al., 1985, In: PCR Technology: Principles and Applications for DNA Amplification (Erlich, ed.) pp. 105–111 (Stockton, New York). The 5' ends of the PCR derived clones were very similar (within 3 bp) to the 5' ends of clones obtained from the cDNA library, suggesting that the 5' end of the hMDM2 sequence shown in FIG. 1 may represent the 5' end of the transcript. Third, in vitro translation of the sequence shown in FIG. 1, beginning with the methionine encoded by the nucleotide 312 ATG, generated a protein similar in size to that observed in human cells.

In FIG. 1, hMDM2 and mMDM2 nucleotide and amino acid sequences are compared. The mouse sequence is only shown where it differs from the corresponding human sequence. Asterisks mark the 5' and 3' boundaries of the previously published mMDM2 cDNA. Fakharzadeh et al., 1991, EMBO J. 10:1565–1569. Dashes indicate insertions. The mouse and human amino acid sequences are compared from the putative translation start site at nucleotide 312 through the conserved stop codon at nucleotide 1784.

Comparison of the human and mouse MDM2 coding regions revealed significant conservation at the nucleotide (80.3%) and amino acid (80.4%) levels. Although hMDM2 and mMDM2 bore little similarity to other genes recorded in current databases, the two proteins shared several motifs. These included a basic nuclear localization signal (Tanaka, 1990, FEBS Letters 271:4146) at codons 181 to 185, several casein kinase II serine phosphorylation sites (Pinna, 1990, Biochem. et. Biophys. Acta. 1054:267–284) at codons 166 to 169, 192 to 195, 269 to 272, and 290 to 293, an acidic activation domain (Ptashne, 1988, Nature 355:683–689) at codons 223 to 274, and two metal binding sites (Harrison, 1991, Nature 353:715) at codons 305 to 322 and 461 to 478, neither of which is highly related to known DNA binding domains. The protein kinase A domain noted in mMDM2 (Fakharzadeh et al., 1991, EMBO J. 10:1565–1569) was not conserved in hMDM2.

EXAMPLE 2

To determine whether the hMDM2 protein could bind to human p53 protein in vitro, an hMDM2 expression vector was constructed from the cDNA clones. The hMDM2 expression vector was constructed in pBluescript SK+ (Stratagene) from overlapping cDNA clones. The construct contained the sequence shown in FIG. 1 from nucleotide 312 to 2176. A 42 bp black beetle virus ribosome entry sequence (Dasmahapatra et al., 1987, Nucleic Acid Research 15:3933) was placed immediately upstream of this hMDM2 sequence in order to obtain a high level of expression. This construct, as well as p53 (El-Deriy et al., 1992, Nature Genetics, in press) and MCC (Kinzler et al., 1991, Science 251:1366–1370)constructs in pBluescript SK+, were transcribed with T7 RNA polymerase and translated in a rabbit reticulocyte lysate (Promega) according to the manufacturer's instructions.

Although the predicted size of the protein generated from the construct was only 55.2 kd (extending from the methionine at nucleotide 312 to nucleotide 1784), in vitro translated protein migrated at approximately 95 kilodaltons.

Ten μl of lysate containing the three proteins (hMDM2, p53 and MCC), alone or mixed in pairs, were incubated at 37° C. for 15 minutes. One microgram (10 μl) of p53 Ab1 (monoclonal antibody specific for the C-terminus of p53) or Ab2 (monoclonal antibody specific for the N-terminus of p53) (Oncogene Science), or 5 μl of rabbit serum containing MDM2 Ab (polyclonal rabbit anti-hMDM2 antibodies) or preimmune rabbit serum (obtained from the rabbit which produced the hMDM2 Ab), were added as indicated. The polyclonal rabbit antibodies were raised against an E. coli-produced hMDM2 -glutathione S-transferase fusion protein containing nucleotides 390 to 816 of the hMDM2 cDNA. Ninety μl of RIPA buffer (10 mM tris [pH 7.5], 1% sodium deoxycholate, 1% NP40, 150 mM NaCl, 0.1% SDS), SNNTE buffer (Levin and George, 1992, submitted for publication), or Binding Buffer (E1-Defiy et al., 1992, Nature Genetics, in press) were then added and the mixtures allowed to incubate at 4° C. for 2 hours.

Two milligrams of protein A sepharose were added to each tube, and the tubes were rotated end-over-end at 4° C. for 1 hour. After pelleting and washing, the immunoprecipitates were subjected to SDS-polyacrylamide gel electrophoresis and the dried gels autoradiographed for 10 to 60 minutes in the presence of Enhance (New England Nuclear).

FIG. 2 shows the co-precipitation of hMDM2 and p53. The three buffers produced similar results, although the co-precipitation was less efficient in SNNTE buffer containing 0.5M NaCl (FIG. 2, lanes 5 and 8) than in Binding Buffer containing 0.1M NaCl (FIG. 2 lanes 6 and 9).

In vitro translated hMDM2, p53 and MCC proteins were mixed as indicated above and incubated with p53 Ab1, p53 Ab2, hMDM2 Ab, or preimmune serum. Lanes 1, 4, 7, 10 and 14 contain aliquots of the protein mixtures used for immunoprecipitation. The bands running slightly faster than p53 are polypeptides produced from internal translation initiation sites.

The hMDM2 protein was not immunoprecipitated with monoclonal antibodies to either the C-terminal or N-terminal regions of p53 (FIG. 2, lanes 2 and 3). However, when in vitro translated human p53 was mixed with the hMDM2 translation product, the anti-p53 antibodies precipitated hMDM2 protein along with p53, demonstrating an association in vitro (FIG. 2, lanes 5 and 6). As a control, a protein of similar electrophoretic mobility from another gene (MCC (Kinzler et al., 1991, Science 251:1366–1370)) was mixed with p53. No co-precipitation of the MCC protein was observed (FIG. 2, lanes 8 and 9). When an in vitro translated mutant form of p53 (175$^{his}$) was mixed with hMDM2 protein, a similar co-precipitation of hMDM2 and p53 proteins was also observed.

In the converse of the experiments described above, the anti-hMDM2 antibodies immunoprecipitated p53 when mixed with hMDM2 protein (FIG. 2, lane 15) but failed to precipitate p53 alone (FIG. 5, lane 13). Preimmune rabbit serum failed to precipitate either hMDM2 or p53 (FIG. 2, lane 16).

EXAMPLE 3

In order to ascertain the chromosomal localization of hMDM2, somatic cell hybrids were screened with an hMDM2 cDNA probe. A human-hamster hybrid containing only human chromosome 12 was found to hybridize to the probe. Screening of hybrids containing portions of chromosome 12 (Turc-Carel et al., 1986, Cancer Genet. Cytogenet. 23:291-299) with the same probe narrowed the localization to chromosome 12q12-14.

EXAMPLE 4

Previous studies have shown that this region of chromosome 12 is often aberrant in human sarcomas. Mandahl et al., 1987, Genes Chromosomes & Cancer 1:9-14; Turc-Carel et al., 1986, Cancer Genet. Cytogenet. 23:291-299; Meltzer et al., 1991, Cell Growth & Differentiation 2:495-501. To evaluate the possibility that hMDM2 was genetically altered in such cancers, Southern blot analysis was performed.

Figure 3:
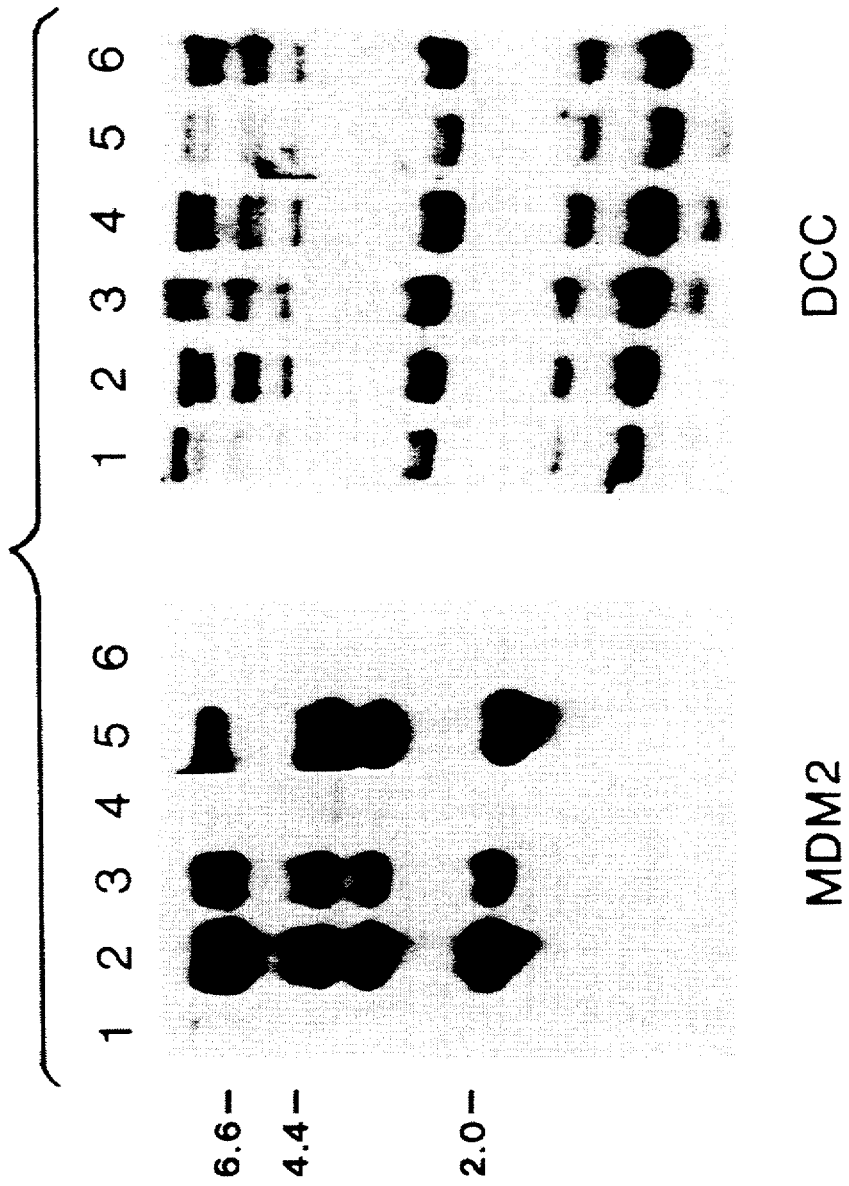
FIG. 3 illustrates the amplification of the hMDM2 gene in sarcomas.

FIG. 3 shows examples of the amplification of the hMDM2 gene in sarcomas. Cellular DNA (5 μg) was digested with EcoRI, separated by agarose gel electrophoresis, and transferred to nylon as described by Reed and Mann (Nucl. Acids Res., 1985, 13:7207-7215). The cellular DNA was derived from five primary sarcomas (lanes 1-4, 6) and one sarcoma cell line (OsA-C1, lane 5). The filters were then hybridized with an hMDM2 cDNA fragment probe nucleotide 1-949 (see FIG. 1), or to a control probe which identifies fragments of similar size (DCC gene, 1.65 cDNA :fragment). Fearon, 1989, Science 247:49-56. Hybridization was performed as described by Vogelstein et al. (Cancer Research, 1987, 47:4806-4813). A striking amplification of hMDM2 sequences was observed in several of these tumors. (See FIG. 3, lanes 2, 3 and 5). Of 47 sarcomas analyzed, 17 exhibited hMDM2 amplification ranging from 5 to 50 fold. These tumors included 7 to 13 liposarcomas, 7 of 22 malignant fibrous histiocytomas (MFH), 3 of 11 osteosarcomas, and 0 and 1 rhabdomyosarcomas. Five benign soft tissue tumors (lipomas) and twenty-seven carcinomas (colorectal or gastric) were also tested by Southern blot analysis and no amplification was observed.

EXAMPLE 5

This example illustrates that gene amplification is associated with increased expression.

Figure 4A:
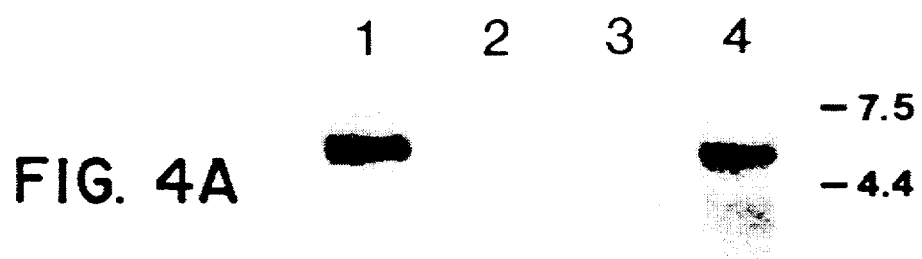
FIG. 4A–C illustrates hMDM2 expression.

FIG. 4A illustrates hMDM2 expression as demonstrated by Northern blot analysis. Because of RNA degradation in the primary sarcomas, only the cell lines could be productively analyzed by Northern blot. RNA was separated by electrophoresis in a MOPS-formaldehyde gel and electrophoretically transferred to nylon filters. Transfer and hybridization were performed as described by Kinzler et al. (Nature, 1988, 332:371-374). The RNA was hybridized to the hMDM2 fragment described in FIG. 3. Ten μg of total RNA derived, respectively, from two sarcoma cell lines (OsA-CL, lane 1 and RC13, lane 2) and the colorectal cancer cell line (CaCo-2) used to make the cDNA library (lane 3). Lane 4 contains 10 μg of polyadenylated CaCo-2 RNA. RNA sizes are shown in kb. In the one available sarcoma cell line with hMDM2 amplification, a single transcript of approximately 5.5 kb was observed (FIG. 4A, lane 1). The amount of this transcript was much higher than in a sarcoma cell line without amplification (FIG. 4A, lane 2) or in a carcinoma cell line (FIG. 4A, lane 3). When purified mRNA (rather than total RNA) from the carcinoma cell line was used for analysis, an hMDM2 transcript of 5.5 kb could also be observed (FIG. 4A, lane 4).

Figure 4B:
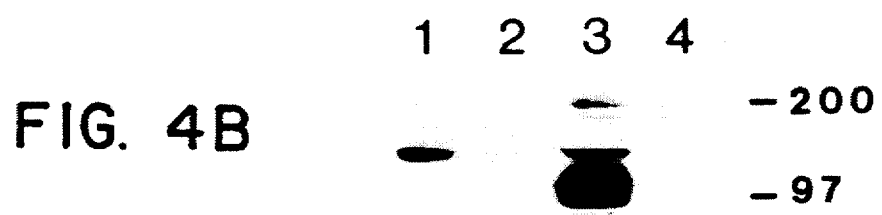

FIG. 4B illustrates hMDM2 expression as demonstrated by Western blot analysis of the sarcoma cell lines RC13 (lane 1), OsA-CL (lane 3), HOS (lane 4), and the carcinoma cell line CaCo-2 (lane 2).

Figure 4C:
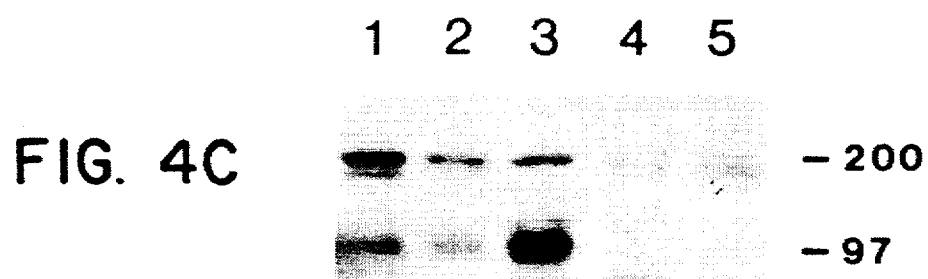

FIG. 4C illustrates hMDM2 expression as demonstrated by Western blot analysis of primary sarcomas. Lanes 1 to 3 contain protein from sarcomas with hMDM2 amplifications, and lanes 4 and 5 contain protein from sarcomas without hMDM2 amplification.

Western blots using affinity purified MDM2 Ab were performed with 50 μg protein per lane as described by Kinzler et al. (Mol. Cell. Biol., 1990, 10:634-642), except that the membranes were blocked in 10% nonfat dried milk and 10% goat serum, and secondary antibodies were coupled to horseradish peroxidase, permitting chemiluminescent detection (Amersham ECL). MDM2 Ab was affinity purified with a pATH-hMDM2 fusion protein using methods described in Kinzler et al. (Mol. Cell. Biol., 1990, 10:634-642). Nonspecifically reactive proteins of 85, 120 and 200 kd were observed in all lanes, irrespective of hMDM2 amplification status. hMDM2 proteins, of 97 kd, were observed only in the hMDM2-amplified tumors. Protein marker sizes are shown in kd.

A protein of approximately 97 kilodaltons was expressed at high levels in the sarcoma cell line with hMDM2 amplification (FIG. 4B, lane 3), whereas no expression was evident in two sarcoma cell lines without amplification or in the carcinoma cell line (FIG. 4B, lanes 1, 2 and 4). Five primary sarcomas were also examined by Western blot analysis. Three primary sarcomas with amplification expressed the same size protein as that observed in the sarcoma cell line (FIG. 4C, lanes 1-3), while no protein was observed in the two sarcomas without amplification (FIG. 4C, lanes 4 and 5).

Expression of the hMDM2 RNA in the sarcoma with amplification was estimated to be at least 30 fold higher than that in the other lines examined. This was consistent with the results of Western blot analysis.

The above examples demonstrate that hMDM2 binds to p53 in vitro and is genetically altered (i.e., amplified) in a significant fraction of sarcomas, including MFH, liposarcomas, and osteosarcomas. These are the most common sarcomas of soft tissue and bone. Weiss and Enzinger, 1978, Cancer 41:2250-2266; Malawer et al., 1985, In: Cancer: Principles and Practice of Oncology, DeVita et al., Eds., pp. 1293-1342 (Lippincott, Pa.).

Human MDM2 amplification is useful for understanding the pathogenesis of these often lethal cancers.

MDM2 may functionally inactivate p53 in ways similar to those employed by virally encoded oncoproteins such as SV40 T-antigen, adenovirus E1B, and HPV E6. Lane and Bechimol, 1990, Genes and Development 4:1-8; Werness et al., 1990, Science 248:76. Consistent with this hypothesis, no sarcomas with hMDM2 amplification had any of the p53 gene mutations that occur commonly in other tumors. hMDM2 amplification provides a parallel between viral carcinogenesis and the naturally occurring genetic alterations underlying sporadic human cancer. The finding that expression of hMDM2 is correspondingly elevated in tumors with amplification of the gene are consistent with the finding that MDM2 binds to p53, and with the hypothesis that overexpression of MDM2 in sarcomas allows escape from p53 regulated growth control. This mechanism of tumorigenesis has striking parallels to that previously observed for virally induced tumors (Lane and Be-chimol, 1990, Genes and Development 4:1-8; Werness et al., 1990, Science 248:76), in which vital oncogene products bind to and functionally inactivate p53.

---

We claim:

1. A method of screening for a neoplastic tissue in a human comprising:
   detecting amplification of a human MDM2 gene or elevated expression of a human MDM2 gene by detecting human MOM2 mRNA in a tissue or body fluid isolated from a human, wherein amplification of the human MDM2 gene or elevated expression of the human MDM2 gene provides a method of screening for neoplasia or the potential for neoplastic development.

2. The method of claim 1 wherein gene amplification is detected.

3. The method of claim 1 wherein said mRNA is detected by Northern blot analysis by hybridizing mRNA from said tissue to a human MDM2 nucleotide probe.

4. The method of claim 3 wherein the human MDM2 nucleotide probe comprises nucleotides 1-2372 of human MDM2, as shown in FIG. 1, or fragments thereof consisting of at least 14 contiguous nucleotides.

5. The method of claim 2 wherein the gene amplification is detected using polymerase chain reaction.

6. The method of claim 2 wherein amplification of the human MDM2 gene is detected by Southern blot analysis wherein the human MDM2 gene is hybridized with a nucleotide probe which is complementary to hMDM2 DNA.

7. The method of claim 2 wherein gene amplification is determined by comparing the copy number of hMDM2 in the tissue to the copy number of hMDM2 in a normal tissue of the human.

8. The method of claim 1 wherein elevated expression of a human MDM2 gene is determined by comparing the amount of hMDM2 mRNA in the tissue to the amount of hMDM2 mRNA in a normal tissue of the human.

9. The method of claim 2 wherein gene amplification is detected when at least 3-fold more hMDM-2 DNA is observed in the tissue relative to a control sample comprising a normal tissue.

10. The method of claim 1 wherein elevated expression is detected when at least 3-fold more hMDM-2 mRNA is observed in the tissue relative to a control sample comprising a normal tissue.

11. The method of claim 1 wherein the neoplasia is a sarcoma.

12. The method of claim 11 wherein the sarcoma is a liposarcoma, malignant fibrous histiocytoma, or osteosarcoma.

* * * * *

UNITED STATES PATENT AND TRADEMARK OFFICE
CERTIFICATE OF CORRECTION

PATENT NO. : 5,411,860
DATED : May 2, 1995
INVENTOR(S) : Bert Vogelstein and Kenneth Kinzler It is certified that error appears in the above-indentified patent and that said Letters Patent is hereby corrected as shown below:

At column 1, line 3 insert the following:

"This invention was made with government support under Grant CA43460, CA35494 and CA41183 awarded by the National Institutes of Health. The government has certain rights in this invention."

Signed and Sealed this

Fifth Day of August, 1997

Attest:

BRUCE LEHMAN

Attesting Officer

Commissioner of Patents and Trademarks

SEQUENCE LISTING ( 1 ) GENERAL INFORMATION:

( i i i ) NUMBER OF SEQUENCES: 4

( 2 ) INFORMATION FOR SEQ ID NO:1:

( i ) SEQUENCE CHARACTERISTICS:
        ( A ) LENGTH: 2372 base pairs
        ( B ) TYPE: nucleic acid
        ( C ) STRANDEDNESS: double
        ( D ) TOPOLOGY: linear ( i i ) MOLECULE TYPE: cDNA ( i i i ) HYPOTHETICAL: NO ( i v ) ANTI-SENSE: NO ( v i ) ORIGINAL SOURCE:
        ( A ) ORGANISM: Homo sapiens
        ( H ) CELL LINE: CaCo-2

( v i i i ) POSITION IN GENOME:
        ( B ) MAP POSITION: 12q12-14

( i x ) FEATURE:
        ( A ) NAME/KEY: CDS
        ( B ) LOCATION: 312..1784

( x i ) SEQUENCE DESCRIPTION: SEQ ID NO:1:

```
GCACCGCGCG  AGCTTGGCTG  CTTCTGGGGC  CTGTGTGGCC  CTGTGTGTCG  GAAAGATGGA        60

GCAAGAAGCC  GAGCCCGAGG  GGCGGCCGCG  ACCCCTCTGA  CCGAGATCCT  GCTGCTTTCG       120

CAGCCAGGAG  CACCGTCCCT  CCCCGGATTA  GTGCGTACGA  GCGCCCAGTG  CCCTGGCCCG       180

GAGAGTGGAA  TGATCCCCGA  GGCCCAGGGC  GTCGTGCTTC  CGCAGTAGTC  AGTCCCCGTG       240

AAGGAAACTG  GGGAGTCTTG  AGGGACCCCC  GACTCCAAGC  GCGAAAACCC  CGGATGGTGA       300

GGAGCAGGCA A  ATG TGC AAT ACC AAC ATG TCT GTA CCT ACT GAT GGT GCT           350
             Met Cys Asn Thr Asn Met Ser Val Pro Thr Asp Gly Ala
               1               5                  10

GTA ACC ACC TCA CAG ATT CCA GCT TCG GAA CAA GAG ACC CTG GTT AGA             398
Val Thr Thr Ser Gln Ile Pro Ala Ser Glu Gln Glu Thr Leu Val Arg
     15                  20                  25

CCA AAG CCA TTG CTT TTG AAG TTA TTA AAG TCT GTT GGT GCA CAA AAA             446
Pro Lys Pro Leu Leu Leu Lys Leu Leu Lys Ser Val Gly Ala Gln Lys
 30              35                  40                  45

GAC ACT TAT ACT ATG AAA GAG GTT CTT TTT TAT CTT GGC CAG TAT ATT             494
Asp Thr Tyr Thr Met Lys Glu Val Leu Phe Tyr Leu Gly Gln Tyr Ile
                 50                  55                  60

ATG ACT AAA CGA TTA TAT GAT GAG AAG CAA CAA CAT ATT GTA TAT TGT             542
Met Thr Lys Arg Leu Tyr Asp Glu Lys Gln Gln His Ile Val Tyr Cys
             65                  70                  75

TCA AAT GAT CTT CTA GGA GAT TTG TTT GGC GTG CCA AGC TTC TCT GTG             590
Ser Asn Asp Leu Leu Gly Asp Leu Phe Gly Val Pro Ser Phe Ser Val
         80                  85                  90

AAA GAG CAC AGG AAA ATA TAT ACC ATG ATC TAC AGG AAC TTG GTA GTA             638
Lys Glu His Arg Lys Ile Tyr Thr Met Ile Tyr Arg Asn Leu Val Val
     95                 100                 105

GTC AAT CAG CAG GAA TCA TCG GAC TCA GGT ACA TCT GTG AGT GAG AAC             686
Val Asn Gln Gln Glu Ser Ser Asp Ser Gly Thr Ser Val Ser Glu Asn
110                 115                 120                 125
```

-continued

| | | | | | | | | | | | | | | | | |
|---|---|---|---|---|---|---|---|---|---|---|---|---|---|---|---|---|
| AGG | TGT | CAC | CTT | GAA | GGT | GGG | AGT | GAT | CAA | AAG | GAC | CTT | GTA | CAA | GAG | 734 |
| Arg | Cys | His | Leu 130 | Glu | Gly | Gly | Ser | Asp 135 | Gln | Lys | Asp | Leu | Val 140 | Gln | Glu | |
| CTT | CAG | GAA | GAG | AAA | CCT | TCA | TCT | TCA | CAT | TTG | GTT | TCT | AGA | CCA | TCT | 782 |
| Leu | Gln | Glu | Glu 145 | Lys | Pro | Ser | Ser 150 | Ser | His | Leu | Val | Ser 155 | Arg | Pro | Ser | |
| ACC | TCA | TCT | AGA | AGG | AGA | GCA | ATT | AGT | GAG | ACA | GAA | GAA | AAT | TCA | GAT | 830 |
| Thr | Ser | Ser 160 | Arg | Arg | Arg | Ala | Ile 165 | Ser | Glu | Thr | Glu | Glu 170 | Asn | Ser | Asp | |
| GAA | TTA | TCT | GGT | GAA | CGA | CAA | AGA | AAA | CGC | CAC | AAA | TCT | GAT | AGT | ATT | 878 |
| Glu | Leu 175 | Ser | Gly | Glu | Arg | Gln 180 | Arg | Lys | Arg | His | Lys 185 | Ser | Asp | Ser | Ile | |
| TCC | CTT | TCC | TTT | GAT | GAA | AGC | CTG | GCT | CTG | TGT | GTA | ATA | AGG | GAG | ATA | 926 |
| Ser 190 | Leu | Ser | Phe | Asp | Glu 195 | Ser | Leu | Ala | Leu | Cys 200 | Val | Ile | Arg | Glu | Ile 205 | |
| TGT | TGT | GAA | AGA | AGC | AGT | AGC | AGT | GAA | TCT | ACA | GGG | ACG | CCA | TCG | AAT | 974 |
| Cys | Cys | Glu | Arg | Ser 210 | Ser | Ser | Ser | Glu | Ser 215 | Thr | Gly | Thr | Pro | Ser 220 | Asn | |
| CCG | GAT | CTT | GAT | GCT | GGT | GTA | AGT | GAA | CAT | TCA | GGT | GAT | TGG | TTG | GAT | 1022 |
| Pro | Asp | Leu | Asp 225 | Ala | Gly | Val | Ser | Glu 230 | His | Ser | Gly | Asp | Trp 235 | Leu | Asp | |
| CAG | GAT | TCA | GTT | TCA | GAT | CAG | TTT | AGT | GTA | GAA | TTT | GAA | GTT | GAA | TCT | 1070 |
| Gln | Asp | Ser 240 | Val | Ser | Asp | Gln | Phe 245 | Ser | Val | Glu | Phe | Glu 250 | Val | Glu | Ser | |
| CTC | GAC | TCA | GAA | GAT | TAT | AGC | CTT | AGT | GAA | GAA | GGA | CAA | GAA | CTC | TCA | 1118 |
| Leu | Asp | Ser | Glu 255 | Asp | Tyr | Ser | Leu | Ser 260 | Glu | Glu | Gly | Gln | Glu 265 | Leu | Ser | |
| GAT | GAA | GAT | GAT | GAG | GTA | TAT | CAA | GTT | ACT | GTG | TAT | CAG | GCA | GGG | GAG | 1166 |
| Asp | Glu | Asp | Asp 270 | Glu | Val | Tyr | Gln | Val 275 | Thr | Val | Tyr | Gln | Ala 280 | Gly | Glu 285 | |
| AGT | GAT | ACA | GAT | TCA | TTT | GAA | GAA | GAT | CCT | GAA | ATT | TCC | TTA | GCT | GAC | 1214 |
| Ser | Asp | Thr | Asp | Ser 290 | Phe | Glu | Glu | Asp | Pro 295 | Glu | Ile | Ser | Leu | Ala 300 | Asp | |
| TAT | TGG | AAA | TGC | ACT | TCA | TGC | AAT | GAA | ATG | AAT | CCC | CCC | CTT | CCA | TCA | 1262 |
| Tyr | Trp | Lys | Cys 305 | Thr | Ser | Cys | Asn | Glu 310 | Met | Asn | Pro | Pro | Leu 315 | Pro | Ser | |
| CAT | TGC | AAC | AGA | TGT | TGG | GCC | CTT | CGT | GAG | AAT | TGG | CTT | CCT | GAA | GAT | 1310 |
| His | Cys | Asn | Arg 320 | Cys | Trp | Ala | Leu | Arg 325 | Glu | Asn | Trp | Leu | Pro 330 | Glu | Asp | |
| AAA | GGG | AAA | GAT | AAA | GGG | GAA | ATC | TCT | GAG | AAA | GCC | AAA | CTG | GAA | AAC | 1358 |
| Lys | Gly | Lys 335 | Asp | Lys | Gly | Glu | Ile 340 | Ser | Glu | Lys | Ala | Lys 345 | Leu | Glu | Asn | |
| TCA | ACA | CAA | GCT | GAA | GAG | GGC | TTT | GAT | GTT | CCT | GAT | TGT | AAA | AAA | ACT | 1406 |
| Ser 350 | Thr | Gln | Ala | Glu | Glu 355 | Gly | Phe | Asp | Val | Pro 360 | Asp | Cys | Lys | Lys | Thr 365 | |
| ATA | GTG | AAT | GAT | TCC | AGA | GAG | TCA | TGT | GTT | GAG | GAA | AAT | GAT | GAT | AAA | 1454 |
| Ile | Val | Asn | Asp | Ser 370 | Arg | Glu | Ser | Cys | Val 375 | Glu | Glu | Asn | Asp | Asp 380 | Lys | |
| ATT | ACA | CAA | GCT | TCA | CAA | TCA | CAA | GAA | AGT | GAA | GAC | TAT | TCT | CAG | CCA | 1502 |
| Ile | Thr | Gln | Ala 385 | Ser | Gln | Ser | Gln | Glu 390 | Ser | Glu | Asp | Tyr | Ser 395 | Gln | Pro | |
| TCA | ACT | TCT | AGT | AGC | ATT | ATT | TAT | AGC | AGC | CAA | GAA | GAT | GTG | AAA | GAG | 1550 |
| Ser | Thr | Ser 400 | Ser | Ser | Ile | Ile | Tyr 405 | Ser | Ser | Gln | Glu | Asp 410 | Val | Lys | Glu | |
| TTT | GAA | AGG | GAA | GAA | ACC | CAA | GAC | AAA | GAA | GAG | AGT | GTG | GAA | TCT | AGT | 1598 |
| Phe | Glu | Arg 415 | Glu | Glu | Thr | Gln | Asp 420 | Lys | Glu | Glu | Ser | Val 425 | Glu | Ser | Ser | |
| TTG | CCC | CTT | AAT | GCC | ATT | GAA | CCT | TGT | GTG | ATT | TGT | CAA | GGT | CGA | CCT | 1646 |
| Leu | Pro 430 | Leu | Asn | Ala | Ile | Glu 435 | Pro | Cys | Val | Ile | Cys 440 | Gln | Gly | Arg | Pro 445 | |
| AAA | AAT | GGT | TGC | ATT | GTC | CAT | GGC | AAA | ACA | GGA | CAT | CTT | ATG | GCC | TGC | 1694 |
| Lys | Asn | Gly | Cys | Ile | Val | His | Gly | Lys | Thr | Gly | His | Leu | Met | Ala | Cys | |

|     |     |     |     |     |     | 450 |     |     |     |     | 455 |     |     |     |     | 460 |     |     |      |
| --- | --- | --- | --- | --- | --- | --- | --- | --- | --- | --- | --- | --- | --- | --- | --- | --- | --- | --- | ---- |
| TTT | ACA | TGT | GCA | AAG | AAG | CTA | AAG | AAA | AGG | AAT | AAG | CCC | TGC | CCA | GTA |     |     |     | 1742 |
| Phe | Thr | Cys | Ala | Lys | Lys | Leu | Lys | Lys | Arg | Asn | Lys | Pro | Cys | Pro | Val |     |     |     |      |
|     |     |     | 465 |     |     |     | 470 |     |     |     |     | 475 |     |     |     |     |     |     |      |
| TGT | AGA | CAA | CCA | ATT | CAA | ATG | ATT | GTG | CTA | ACT | TAT | TTC | CCC |     |     |     |     |     | 1784 |
| Cys | Arg | Gln | Pro | Ile | Gln | Met | Ile | Val | Leu | Thr | Tyr | Phe | Pro |     |     |     |     |     |      |
|     |     | 480 |     |     |     | 485 |     |     |     |     | 490 |     |     |     |     |     |     |     |      |

```
TAGTTGACCT  GTCTATAAGA  GAATTATATA  TTTCTAACTA  TATAACCCTA  GGAATTTAGA   1844
CAACCTGAAA  TTTATTCACA  TATATCAAAG  TGAGAAAATG  CCTCAATTCA  CATAGATTTC   1904
TTCTCTTTAG  TATAATTGAC  CTACTTTGGT  AGTGGAATAG  TGAATACTTA  CTATAATTTG   1964
ACTTGAATAT  GTAGCTCATC  CTTTACACCA  ACTCCTAATT  TTAAATAATT  TCTACTCTGT   2024
CTTAAATGAG  AAGTACTTGG  TTTTTTTTTT  CTTAAATATG  TATATGACAT  TTAAATGTAA   2084
CTTATTATTT  TTTTGAGAC   CGAGTCTTGC  TCTGTTACCC  AGGCTGGAGT  GCAGTGGGTG   2144
ATCTTGGCTC  ACTGCAAGCT  CTGCCCTCCC  CGGGTTCGCA  CCATTCTCCT  GCCTCAGCCT   2204
CCCAATTAGC  TTGGCCTACA  GTCATCTGCC  ACCACACCTG  GCTAATTTTT  TGTACTTTTA   2264
GTAGAGACAG  GGTTTCACCG  TGTTAGCCAG  GATGGTCTCG  ATCTCCTGAC  CTCGTGATCC   2324
GCCCACCTCG  GCCTCCCAAA  GTGCTGGGAT  TACAGGCATG  AGCCACCG                 2372
```

( 2 ) INFORMATION FOR SEQ ID NO:2:

( i ) SEQUENCE CHARACTERISTICS:
        ( A ) LENGTH: 491 amino acids
        ( B ) TYPE: amino acid
        ( D ) TOPOLOGY: linear ( i i ) MOLECULE TYPE: protein ( x i ) SEQUENCE DESCRIPTION: SEQ ID NO:2:

```
Met  Cys  Asn  Thr  Asn  Met  Ser  Val  Pro  Thr  Asp  Gly  Ala  Val  Thr
 1                    5                   10                        15

Ser  Gln  Ile  Pro  Ala  Ser  Glu  Gln  Glu  Thr  Leu  Val  Arg  Pro  Lys  Pro
                  20                   25                        30

Leu  Leu  Leu  Lys  Leu  Leu  Lys  Ser  Val  Gly  Ala  Gln  Lys  Asp  Thr  Tyr
              35                   40                        45

Thr  Met  Lys  Glu  Val  Leu  Phe  Tyr  Leu  Gly  Gln  Tyr  Ile  Met  Thr  Lys
 50                         55                        60

Arg  Leu  Tyr  Asp  Glu  Lys  Gln  Gln  His  Ile  Val  Tyr  Cys  Ser  Asn  Asp
 65                    70                        75                        80

Leu  Leu  Gly  Asp  Leu  Phe  Gly  Val  Pro  Ser  Phe  Ser  Val  Lys  Glu  His
                  85                   90                        95

Arg  Lys  Ile  Tyr  Thr  Met  Ile  Tyr  Arg  Asn  Leu  Val  Val  Val  Asn  Gln
              100                  105                       110

Gln  Glu  Ser  Ser  Asp  Ser  Gly  Thr  Ser  Val  Ser  Glu  Asn  Arg  Cys  His
              115                  120                       125

Leu  Glu  Gly  Gly  Ser  Asp  Gln  Lys  Asp  Leu  Val  Gln  Glu  Leu  Gln  Glu
         130                  135                       140

Glu  Lys  Pro  Ser  Ser  Ser  His  Leu  Val  Ser  Arg  Pro  Ser  Thr  Ser  Ser
145                       150                  155                       160

Arg  Arg  Arg  Ala  Ile  Ser  Glu  Thr  Glu  Glu  Asn  Ser  Asp  Glu  Leu  Ser
                  165                  170                       175

Gly  Glu  Arg  Gln  Arg  Lys  Arg  His  Lys  Ser  Asp  Ser  Ile  Ser  Leu  Ser
              180                  185                       190

Phe  Asp  Glu  Ser  Leu  Ala  Leu  Cys  Val  Ile  Arg  Glu  Ile  Cys  Cys  Glu
         195                  200                       205

Arg  Ser  Ser  Ser  Ser  Glu  Ser  Thr  Gly  Thr  Pro  Ser  Asn  Pro  Asp  Leu
```

|     |     |     |     |     |     |     |     |     |     |     |     |     |     |     |
|---|---|---|---|---|---|---|---|---|---|---|---|---|---|---|
|     |     |     |     | 210 |     |     |     | 215 |     |     |     | 220 |     |     |
| Asp<br>225 | Ala | Gly | Val | Ser | Glu<br>230 | His | Ser | Gly | Asp | Trp<br>235 | Leu | Asp | Gln | Asp | Ser<br>240 |
| Val | Ser | Asp | Gln | Phe<br>245 | Ser | Val | Glu | Phe<br>250 | Val | Glu | Ser | Leu | Asp<br>255 | Ser |
| Glu | Asp | Tyr | Ser<br>260 | Leu | Ser | Glu | Glu | Gly<br>265 | Gln | Glu | Leu | Ser | Asp<br>270 | Glu | Asp |
| Asp | Glu | Val<br>275 | Tyr | Gln | Val | Thr | Val<br>280 | Tyr | Gln | Ala | Gly | Glu<br>285 | Ser | Asp | Thr |
| Asp | Ser<br>290 | Phe | Glu | Glu | Asp | Pro<br>295 | Glu | Ile | Ser | Leu | Ala<br>300 | Asp | Tyr | Trp | Lys |
| Cys<br>305 | Thr | Ser | Cys | Asn | Glu<br>310 | Met | Asn | Pro | Pro | Leu<br>315 | Pro | Ser | His | Cys | Asn<br>320 |
| Arg | Cys | Trp | Ala | Leu<br>325 | Arg | Glu | Asn | Trp | Leu<br>330 | Pro | Glu | Asp | Lys | Gly<br>335 | Lys |
| Asp | Lys | Gly | Glu<br>340 | Ile | Ser | Glu | Lys | Ala<br>345 | Lys | Leu | Glu | Asn | Ser<br>350 | Thr | Gln |
| Ala | Glu | Glu<br>355 | Gly | Phe | Asp | Val | Pro<br>360 | Asp | Cys | Lys | Lys | Thr<br>365 | Ile | Val | Asn |
| Asp | Ser<br>370 | Arg | Glu | Ser | Cys | Val<br>375 | Glu | Glu | Asn | Asp | Lys<br>380 | Ile | Thr | Gln |
| Ala<br>385 | Ser | Gln | Ser | Gln | Glu<br>390 | Ser | Glu | Asp | Tyr | Ser<br>395 | Gln | Pro | Ser | Thr | Ser<br>400 |
| Ser | Ser | Ile | Ile | Tyr<br>405 | Ser | Ser | Gln | Glu | Asp<br>410 | Val | Lys | Glu | Phe | Glu<br>415 | Arg |
| Glu | Glu | Thr | Gln<br>420 | Asp | Lys | Glu | Glu | Ser<br>425 | Val | Glu | Ser | Ser | Leu<br>430 | Pro | Leu |
| Asn | Ala | Ile<br>435 | Glu | Pro | Cys | Val | Ile<br>440 | Cys | Gln | Gly | Arg | Pro<br>445 | Lys | Asn | Gly |
| Cys | Ile<br>450 | Val | His | Gly | Lys | Thr<br>455 | Gly | His | Leu | Met | Ala<br>460 | Cys | Phe | Thr | Cys |
| Ala<br>465 | Lys | Lys | Leu | Lys | Lys<br>470 | Arg | Asn | Lys | Pro | Cys<br>475 | Pro | Val | Cys | Arg | Gln<br>480 |
| Pro | Ile | Gln | Met | Ile<br>485 | Val | Leu | Thr | Tyr | Phe<br>490 | Pro |

( 2 ) INFORMATION FOR SEQ ID NO:3:

( i ) SEQUENCE CHARACTERISTICS:
        ( A ) LENGTH: 1710 base pairs
        ( B ) TYPE: nucleic acid
        ( C ) STRANDEDNESS: double
        ( D ) TOPOLOGY: linear ( i i ) MOLECULE TYPE: cDNA ( i i i ) HYPOTHETICAL: NO ( i v ) ANTI-SENSE: NO ( v i ) ORIGINAL SOURCE:
        ( A ) ORGANISM: Mus musculus ( i x ) FEATURE:
        ( A ) NAME/KEY: CDS
        ( B ) LOCATION: 202..1668

( x i ) SEQUENCE DESCRIPTION: SEQ ID NO:3:

| | | | | | |
|---|---|---|---|---|---|
| GAGGAGCCGC | CGCCTTCTCG | TCGCTCGAGC | TCTGGACGAC | CATGGTCGCT | CAGGCCCCGT | 60 |
| CCGCGGGGCC | TCCGCGCTCC | CCGTGAAGGG | TCGGAAGATG | CGCGGGAAGT | AGCAGCCGTC | 120 |
| TGCTGGGCGA | GCGGGAGACC | GACCGGACAC | CCCTGGGGGA | CCCTCTCGGA | TCACCGCGCT | 180 |

```
TCTCCTGCGG CCTCCAGGCC A ATG TGC AAT ACC AAC ATG TCT GTG TCT ACC                231
                        Met Cys Asn Thr Asn Met Ser Val Ser Thr
                         1           5                      10

GAG GGT GCT GCA AGC ACC TCA CAG ATT CCA GCT TCG GAA CAA GAG ACT                279
Glu Gly Ala Ala Ser Thr Ser Gln Ile Pro Ala Ser Glu Gln Glu Thr
             15                  20                  25

CTG GTT AGA CCA AAA CCA TTG CTT TTG AAG TTG TTA AAG TCC GTT GGA                327
Leu Val Arg Pro Lys Pro Leu Leu Leu Lys Leu Leu Lys Ser Val Gly
             30                  35                  40

GCG CAA AAC GAC ACT TAC ACT ATG AAA GAG ATT ATA TTT TAT ATT GGC                375
Ala Gln Asn Asp Thr Tyr Thr Met Lys Glu Ile Ile Phe Tyr Ile Gly
             45                  50                  55

CAG TAT ATT ATG ACT AAG AGG TTA TAT GAC GAG AAG CAG CAG CAC ATT                423
Gln Tyr Ile Met Thr Lys Arg Leu Tyr Asp Glu Lys Gln Gln His Ile
     60                  65                  70

GTG TAT TGT TCA AAT GAT CTC CTA GGA GAT GTG TTT GGA GTC CCG AGT                471
Val Tyr Cys Ser Asn Asp Leu Leu Gly Asp Val Phe Gly Val Pro Ser
 75                  80                  85                  90

TTC TCT GTG AAG GAG CAC AGG AAA ATA TAT GCA ATG ATC TAC AGA AAT                519
Phe Ser Val Lys Glu His Arg Lys Ile Tyr Ala Met Ile Tyr Arg Asn
                 95                 100                 105

TTA GTG GCT GTA AGT CAG CAA GAC TCT GGC ACA TCG CTG AGT GAG AGC                567
Leu Val Ala Val Ser Gln Gln Asp Ser Gly Thr Ser Leu Ser Glu Ser
             110                 115                 120

AGA CGT CAG CCT GAA GGT GGG AGT GAT CTG AAG GAT CCT TTG CAA GCG                615
Arg Arg Gln Pro Glu Gly Gly Ser Asp Leu Lys Asp Pro Leu Gln Ala
             125                 130                 135

CCA CCA GAA GAG AAA CCT TCA TCT TCT GAT TTA ATT TCT AGA CTG TCT                663
Pro Pro Glu Glu Lys Pro Ser Ser Ser Asp Leu Ile Ser Arg Leu Ser
             140                 145                 150

ACC TCA TCT AGA AGG AGA TCC ATT AGT GAG ACA GAA GAG AAC ACA GAT                711
Thr Ser Ser Arg Arg Arg Ser Ile Ser Glu Thr Glu Glu Asn Thr Asp
155                 160                 165                 170

GAG CTA CCT GGG GAG CGG CAC CGG AAG CGC CGC AGG TCC CTG TCC TTT                759
Glu Leu Pro Gly Glu Arg His Arg Lys Arg Arg Arg Ser Leu Ser Phe
                 175                 180                 185

GAT CCG AGC CTG GGT CTG TGT GAG CTG AGG GAG ATG TGC AGC GGC GGC                807
Asp Pro Ser Leu Gly Leu Cys Glu Leu Arg Glu Met Cys Ser Gly Gly
             190                 195                 200

ACG AGC AGC AGT AGC AGC AGC AGC GAG TCC ACA GAG ACG CCC TCG                    855
Thr Ser Ser Ser Ser Ser Ser Ser Glu Ser Thr Glu Thr Pro Ser
             205                 210                 215

CAT CAG GAT CTT GAC GAT GGC GTA AGT GAG CAT TCT GGT GAT TGC CTG                903
His Gln Asp Leu Asp Asp Gly Val Ser Glu His Ser Gly Asp Cys Leu
     220                 225                 230

GAT CAG GAT TCA GTT TCT GAT CAG TTT AGC GTG GAA TTT GAA GTT GAG                951
Asp Gln Asp Ser Val Ser Asp Gln Phe Ser Val Glu Phe Glu Val Glu
235                 240                 245                 250

TCT CTG GAC TCG GAA GAT TAC AGC CTG AGT GAC GAA GGG CAC GAG CTC                999
Ser Leu Asp Ser Glu Asp Tyr Ser Leu Ser Asp Glu Gly His Glu Leu
                 255                 260                 265

TCA GAT GAG GAT GAT GAG GTC TAT CGG GTC ACA GTC TAT CAG ACA GGA               1047
Ser Asp Glu Asp Asp Glu Val Tyr Arg Val Thr Val Tyr Gln Thr Gly
             270                 275                 280

GAA AGC GAT ACA GAC TCT TTT GAA GGA GAT CCT GAG ATT TCC TTA GCT               1095
Glu Ser Asp Thr Asp Ser Phe Glu Gly Asp Pro Glu Ile Ser Leu Ala
             285                 290                 295

GAC TAT TGG AAG TGT ACC TCA TGC AAT GAA ATG AAT CCT CCC CTT CCA               1143
Asp Tyr Trp Lys Cys Thr Ser Cys Asn Glu Met Asn Pro Pro Leu Pro
300                 305                 310
```

| | | | | | | | | | | | | | | | | |
|---|---|---|---|---|---|---|---|---|---|---|---|---|---|---|---|---|
| TCA | CAC | TGC | AAA | AGA | TGC | TGG | ACC | CTT | CGT | GAG | AAC | TGG | CTT | CCA | GAC | 1191 |
| Ser | His | Cys | Lys | Arg | Cys | Trp | Thr | Leu | Arg | Glu | Asn | Trp | Leu | Pro | Asp | |
| 315 | | | | 320 | | | | | 325 | | | | | | 330 | |
| GAT | AAG | GGG | AAA | GAT | AAA | GTG | GAA | ATC | TCT | GAA | AAA | GCC | AAA | CTG | GAA | 1239 |
| Asp | Lys | Gly | Lys | Asp | Lys | Val | Glu | Ile | Ser | Glu | Lys | Ala | Lys | Leu | Glu | |
| | | | | 335 | | | | | 340 | | | | | 345 | | |
| AAC | TCA | GCT | CAG | GCA | GAA | GAA | GGC | TTG | GAT | GTG | CCT | GAT | GGC | AAA | AAG | 1287 |
| Asn | Ser | Ala | Gln | Ala | Glu | Glu | Gly | Leu | Asp | Val | Pro | Asp | Gly | Lys | Lys | |
| | | | 350 | | | | | 355 | | | | | 360 | | | |
| CTG | ACA | GAG | AAT | GAT | GCT | AAA | GAG | CCA | TGT | GCT | GAG | GAG | GAC | AGC | GAG | 1335 |
| Leu | Thr | Glu | Asn | Asp | Ala | Lys | Glu | Pro | Cys | Ala | Glu | Glu | Asp | Ser | Glu | |
| | | 365 | | | | 370 | | | | | 375 | | | | | |
| GAG | AAG | GCC | GAA | CAG | ACG | CCC | CTG | TCC | CAG | GAG | AGT | GAC | GAC | TAT | TCC | 1383 |
| Glu | Lys | Ala | Glu | Gln | Thr | Pro | Leu | Ser | Gln | Glu | Ser | Asp | Asp | Tyr | Ser | |
| | 380 | | | | | 385 | | | | | 390 | | | | | |
| CAA | CCA | TCG | ACT | TCC | AGC | AGC | ATT | GTT | TAT | AGC | AGC | CAA | GAA | AGC | GTG | 1431 |
| Gln | Pro | Ser | Thr | Ser | Ser | Ser | Ile | Val | Tyr | Ser | Ser | Gln | Glu | Ser | Val | |
| 395 | | | | 400 | | | | | 405 | | | | | 410 | | |
| AAA | GAG | TTG | AAG | GAG | GAA | ACG | CAG | CAC | AAA | GAC | GAG | AGT | GTG | GAA | TCT | 1479 |
| Lys | Glu | Leu | Lys | Glu | Glu | Thr | Gln | His | Lys | Asp | Glu | Ser | Val | Glu | Ser | |
| | | | | 415 | | | | | 420 | | | | | 425 | | |
| AGC | TTC | TCC | CTG | AAT | GCC | ATC | GAA | CCA | TGT | GTG | ATC | TGC | CAG | GGG | CGG | 1527 |
| Ser | Phe | Ser | Leu | Asn | Ala | Ile | Glu | Pro | Cys | Val | Ile | Cys | Gln | Gly | Arg | |
| | | | 430 | | | | | 435 | | | | | 440 | | | |
| CCT | AAA | AAT | GGC | TGC | ATT | GTT | CAC | GGC | AAG | ACT | GGA | CAC | CTC | ATG | TCA | 1575 |
| Pro | Lys | Asn | Gly | Cys | Ile | Val | His | Gly | Lys | Thr | Gly | His | Leu | Met | Ser | |
| | | 445 | | | | | 450 | | | | | 455 | | | | |
| TGT | TTC | ACG | TGT | GCA | AAG | AAG | CTA | AAA | AAA | AGA | AAC | AAG | CCC | TGC | CCA | 1623 |
| Cys | Phe | Thr | Cys | Ala | Lys | Lys | Leu | Lys | Lys | Arg | Asn | Lys | Pro | Cys | Pro | |
| | | 460 | | | | 465 | | | | | 470 | | | | | |
| GTG | TGC | AGA | CAG | CCA | ATC | CAA | ATG | ATT | GTG | CTA | AGT | TAC | TTC | AAC | | 1668 |
| Val | Cys | Arg | Gln | Pro | Ile | Gln | Met | Ile | Val | Leu | Ser | Tyr | Phe | Asn | | |
| 475 | | | | 480 | | | | | 485 | | | | | | | |
| TAGCTGACCT | GCTCACAAAA | ATAGAATTTT | ATATTTCTAA | CT | | | | | | | | | | | | 1710 |

( 2 ) INFORMATION FOR SEQ ID NO:4:

( i ) SEQUENCE CHARACTERISTICS:
        ( A ) LENGTH: 489 amino acids
        ( B ) TYPE: amino acid
        ( D ) TOPOLOGY: linear ( i i ) MOLECULE TYPE: protein ( x i ) SEQUENCE DESCRIPTION: SEQ ID NO:4:

| | | | | | | | | | | | | | | |
|---|---|---|---|---|---|---|---|---|---|---|---|---|---|---|
| Met | Cys | Asn | Thr | Asn | Met | Ser | Val | Ser | Thr | Glu | Gly | Ala | Ala | Ser | Thr |
| 1 | | | | 5 | | | | | 10 | | | | | 15 | |
| Ser | Gln | Ile | Pro | Ala | Ser | Glu | Gln | Glu | Thr | Leu | Val | Arg | Pro | Lys | Pro |
| | | | 20 | | | | | 25 | | | | | 30 | | |
| Leu | Leu | Leu | Lys | Leu | Leu | Lys | Ser | Val | Gly | Ala | Gln | Asn | Asp | Thr | Tyr |
| | | 35 | | | | | 40 | | | | | 45 | | | |
| Thr | Met | Lys | Glu | Ile | Ile | Phe | Tyr | Ile | Gly | Gln | Tyr | Ile | Met | Thr | Lys |
| | 50 | | | | | 55 | | | | | 60 | | | | |
| Arg | Leu | Tyr | Asp | Glu | Lys | Gln | Gln | His | Ile | Val | Tyr | Cys | Ser | Asn | Asp |
| 65 | | | | | 70 | | | | | 75 | | | | | 80 |
| Leu | Leu | Gly | Asp | Val | Phe | Gly | Val | Pro | Ser | Phe | Ser | Val | Lys | Glu | His |
| | | | | 85 | | | | | 90 | | | | | 95 | |
| Arg | Lys | Ile | Tyr | Ala | Met | Ile | Tyr | Arg | Asn | Leu | Val | Ala | Val | Ser | Gln |
| | | | 100 | | | | | 105 | | | | | 110 | | |
| Gln | Asp | Ser | Gly | Thr | Ser | Leu | Ser | Glu | Ser | Arg | Arg | Gln | Pro | Glu | Gly |
| | | 115 | | | | | 120 | | | | | 125 | | | |

| | | | | | | | | | | | | | | |
|---|---|---|---|---|---|---|---|---|---|---|---|---|---|---|
| Gly | Ser 130 | Asp | Leu | Lys | Asp | Pro 135 | Leu | Gln | Ala | Pro | Pro 140 | Glu | Glu | Lys | Pro |
| Ser 145 | Ser | Ser | Asp | Leu | Ile 150 | Ser | Arg | Leu | Ser | Thr 155 | Ser | Ser | Arg | Arg | Arg 160 |
| Ser | Ile | Ser | Glu | Thr 165 | Glu | Glu | Asn | Thr | Asp 170 | Glu | Leu | Pro | Gly | Glu 175 | Arg |
| His | Arg | Lys | Arg 180 | Arg | Arg | Ser | Leu | Ser 185 | Phe | Asp | Pro | Ser | Leu 190 | Gly | Leu |
| Cys | Glu | Leu 195 | Arg | Glu | Met | Cys | Ser 200 | Gly | Gly | Thr | Ser | Ser 205 | Ser | Ser | Ser |
| Ser | Ser 210 | Ser | Glu | Ser | Thr | Glu 215 | Thr | Pro | Ser | His | Gln 220 | Asp | Leu | Asp | Asp |
| Gly 225 | Val | Ser | Glu | His | Ser 230 | Gly | Asp | Cys | Leu | Asp 235 | Gln | Asp | Ser | Val | Ser 240 |
| Asp | Gln | Phe | Ser | Val 245 | Glu | Phe | Glu | Val | Glu 250 | Ser | Leu | Asp | Ser | Glu 255 | Asp |
| Tyr | Ser | Leu | Ser 260 | Asp | Glu | Gly | His | Glu 265 | Leu | Ser | Asp | Glu | Asp 270 | Asp | Glu |
| Val | Tyr | Arg 275 | Val | Thr | Val | Tyr | Gln 280 | Thr | Gly | Glu | Ser | Asp 285 | Thr | Asp | Ser |
| Phe | Glu 290 | Gly | Asp | Pro | Glu | Ile 295 | Ser | Leu | Ala | Asp | Tyr 300 | Trp | Lys | Cys | Thr |
| Ser 305 | Cys | Asn | Glu | Met | Asn 310 | Pro | Pro | Leu | Pro | Ser 315 | His | Cys | Lys | Arg | Cys 320 |
| Trp | Thr | Leu | Arg | Glu 325 | Asn | Trp | Leu | Pro | Asp 330 | Asp | Lys | Gly | Lys | Asp 335 | Lys |
| Val | Glu | Ile | Ser 340 | Glu | Lys | Ala | Lys | Leu 345 | Glu | Asn | Ser | Ala | Gln 350 | Ala | Glu |
| Glu | Gly | Leu 355 | Asp | Val | Pro | Asp | Gly 360 | Lys | Lys | Leu | Thr | Glu 365 | Asn | Asp | Ala |
| Lys | Glu 370 | Pro | Cys | Ala | Glu | Glu 375 | Asp | Ser | Glu | Glu | Lys 380 | Ala | Glu | Gln | Thr |
| Pro 385 | Leu | Ser | Gln | Glu | Ser 390 | Asp | Asp | Tyr | Ser | Gln 395 | Pro | Ser | Thr | Ser | Ser 400 |
| Ser | Ile | Val | Tyr | Ser 405 | Ser | Gln | Glu | Ser | Val 410 | Lys | Glu | Leu | Lys | Glu 415 | Glu |
| Thr | Gln | His | Lys 420 | Asp | Glu | Ser | Val | Glu 425 | Ser | Ser | Phe | Ser | Leu 430 | Asn | Ala |
| Ile | Glu | Pro 435 | Cys | Val | Ile | Cys | Gln 440 | Gly | Arg | Pro | Lys | Asn 445 | Gly | Cys | Ile |
| Val | His 450 | Gly | Lys | Thr | Gly | His 455 | Leu | Met | Ser | Cys | Phe 460 | Thr | Cys | Ala | Lys |
| Lys 465 | Leu | Lys | Lys | Arg | Asn 470 | Lys | Pro | Cys | Pro | Val 475 | Cys | Arg | Gln | Pro | Ile 480 |
| Gln | Met | Ile | Val | Leu 485 | Ser | Tyr | Phe | Asn | | | | | | | |